United States Patent
Nair et al.

(10) Patent No.: US 10,934,233 B2
(45) Date of Patent: Mar. 2, 2021

(54) GAS PHASE PROCESS FOR CHLOROTRIFLUOROETHYLENE

(71) Applicant: HONEYWELL INTERNATIONAL INC., Morris Plains, NJ (US)

(72) Inventors: Haridasan K. Nair, Williamsville, NY (US); Rajiv Ratna Singh, Getzville, NY (US); Glenn Matthies, Lockport, NY (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 16/267,722

(22) Filed: Feb. 5, 2019

(65) Prior Publication Data
US 2019/0241489 A1 Aug. 8, 2019

Related U.S. Application Data

(60) Provisional application No. 62/626,212, filed on Feb. 5, 2018.

(51) Int. Cl.
*C07C 17/23* (2006.01)
(52) U.S. Cl.
CPC .................. *C07C 17/23* (2013.01)
(58) Field of Classification Search
CPC ......... C07C 17/10; C07C 17/23; C07C 21/06; C07C 21/18
See application file for complete search history.

(56) References Cited

U.S. PATENT DOCUMENTS

| | | | | | |
|---|---|---|---|---|---|
| 4,155,941 | A | * | 5/1979 | Nychka | C07C 17/10 570/156 |
| 4,226,812 | A | * | 10/1980 | Pieters | C07C 17/23 502/60 |
| 2016/0068455 | A1 | | 3/2016 | Wang et al. | |

FOREIGN PATENT DOCUMENTS

| | | |
|---|---|---|
| EP | 0416615 | 3/1993 |
| JP | H05-194289 | 8/1993 |

OTHER PUBLICATIONS

PCT/US2019/016602—International Search Report.

* cited by examiner

*Primary Examiner* — Jafar F Parsa
(74) *Attorney, Agent, or Firm* — Roberts & Roberts, LLP; Richard S. Roberts, Jr.

(57) ABSTRACT

The present invention relates to a process for the preparation of haloethylenes, and preferably perhaloethylenes, by the gas-phase dechlorination of haloethanes in the presence of a catalyst and optionally in the presence of an alkene or an alkane. In particular aspects, the invention relates to a gas-phase process for preparing chlorotrifluoroethylene (CTFE). More particularly, the present invention relates to a gas-phase process for preparing CTFE from 1,1,2-trichloro-1,2,2-trifluoroethane (CFC-113) by dechlorination in the presence of an alkene or an alkane and a catalyst.

20 Claims, No Drawings

GAS PHASE PROCESS FOR CHLOROTRIFLUOROETHYLENE

CROSS REFERENCE TO RELATED APPLICATIONS

This application relates to and claims the priority benefit of U.S. Provisional Application 62/626,212 filed Feb. 5, 2018, which is incorporated herein by reference.

FIELD OF THE INVENTION

The present invention relates to a process for the preparation of haloethylenes, and preferably perhaloethylenes, by the dechlorination of haloethanes comprising reacting in the gaseous phase a haloethane in the presence of a catalyst. In particular aspects, the invention relates to a gas-phase process for preparing chlorotrifluoroethylene ("CTFE"). More particularly, the present invention relates to a gas-phase process for preparing CTFE from 1,1,2-trichloro-1,2,2-trifluoroethane ("CFC-113") by dechlorination in the presence of a catalyst.

BACKGROUND

CTFE is a commercially important monomer in the production of fluoropolymers.

Various methods have been used to prepare CTFE. These methods have suffered from certain disadvantages including consumption of expensive materials, low product yield or both. For example, CTFE has been prepared by a liquid phase process comprising dechlorinating 1,1,2-trichloro-1,2,2-trifluoroethane with zinc. Although CTFE can be obtained by this process in good yield, treatment of the zinc chloride by-product is troublesome and expensive. CTFE has also been prepared by the co-pyrolysis of dichlorofluoromethane and chlorodifluoromethane. However, the co-pyrolysis provided the CTFE in a low yield.

CTFE has been prepared by the gas phase dechlorination of 1,1,2-trichloro-1,2,2-trifluoroethane with hydrogen in the presence of various active carbon catalysts. In the gas phase process using active carbon, a space velocity cannot be larger than about 500 hr$^{-1}$ resulting in low productivity. A gas phase dechlorination using a Pd catalyst has been suggested, but Pd is expensive and deactivated in a short reaction time, and the reaction carried out at a contact time of 10 to 60 seconds, so that the productivity is low. Also, the yield of CTFE these catalysts was unsatisfactory.

The preparation of CTFE using a gas phase dechlorination process is disclosed in U.S. Pat. No. 4,155,941. The main disadvantages of this process are reduced conversion of the starting material, low yield of the CTFE product and/or the formation of undesired material ($CF_2=CCl_2$) in significant amount (>70% in some cases with $Al_2O_3/FeCl_3$ catalyst).

Applicants have therefore come to appreciate a continuing need in the art for further improvements in processes for the production of CTFE. The present invention provides processes that result in the production of haloethylenes, and preferably perhaloethylenes, and most preferably CTFE in good selectivity and conversion, while remaining cost effective from a materials and equipment standpoint.

SUMMARY OF THE INVENTION

The present invention provides a method for the production of haloethylenes, and preferably perhaloethylenes comprising dechlorinating one or more haloethanes in the gaseous phase in the present of a catalyst and at least compound that will react in the gaseous reaction mixture with chlorine from the dechlorination reaction, preferably an alkene or an alkane in the presence of a catalyst.

The invention also provides a gas phase process for the production of CTFE comprising reacting in the gas phase 1,1,2-trichloro-1,2,2-trifluoroethane ($CF_2Cl$—$CFCl_2$; CFC-113) and at least one of an alkane (such as methane, ethane, propane, isobutane, etc.) or alkene (such as ethylene, propylene, butylene, etc.) in the presence of a catalyst. For the purpose of convenience, methods according to this paragraph are sometime referred to herein as Method 1.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and at least on of an alkane (such as methane, ethane, propane, isobutane, etc.); and (b) reacting said reaction mixture in the presence of a catalyst. For the purpose of convenience, methods according to this paragraph are sometime referred to herein as Method 2.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and at least on of an alkane (such as methane, ethane, propane, isobutane, etc.) or alkene (such as ethylene, propylene, butylene, etc.); and (b) reacting said reaction mixture in the presence of a catalyst at a temperature of from about 300° C. to about 600° C. For the purpose of convenience, methods according to this paragraph are sometime referred to herein as Method 3.

As used herein in connection with reaction temperatures, the term "about" means the indicated temperature +/−10° C.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and at least on of an alkane (such as methane, ethane, propane, isobutane, etc.) or alkene (such as ethylene, propylene, butylene, etc.); (b) providing a reactor containing catalyst; and (c) reacting said reaction mixture in said reactor in the presence of said catalyst at a temperature of from about 400° C. to about 600° C. For the purpose of convenience, methods according to this paragraph are sometime referred to herein as Method 4.

The invention also provides a gas phase process for the production of CTFE comprising reacting in the gas phase 1,1,2-trichloro-1,2,2-trifluoroethane ($CF_2Cl$—$CFCl_2$; CFC-113) and an alkane having from 1 to 3 carbon atoms in the presence of a catalyst. For the purpose of convenience, methods according to this paragraph are sometime referred to herein as Method 5. For the purpose of convenience, alkanes having from 1 to 3 carbon atoms are referred to herein for convenience as "C1-C3" alkanes.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 3 carbon atoms; and (b) reacting said reaction mixture in the presence of a catalyst. For the purpose of convenience, methods according to this paragraph are sometime referred to herein as Method 6.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and a C1-C3 alkane; and (b) reacting said reaction mixture in the presence of a catalyst at a temperature of from about 400° C. to about 600° C. For the purpose of convenience, methods according to this paragraph are sometime referred to herein as Method 7.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and a C1-C3 alkane, wherein said reaction mixture comprises less than 1% by weight of alkanes and is substantially free of 1,1,1-trichloro-2,2,2-trifluoroethane (CFC-113a); and (b) reacting said reaction mixture in the presence of a catalyst at a temperature of from about 400° C. to about 600° C. For the purpose of convenience, methods according to this paragraph are sometime referred to herein as Method 8.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 6 carbon atoms; and (b) reacting said reaction mixture in the presence of a catalyst to produce a reaction product that comprises at least about 74% of CTFE and is substantially free of 2-chloro-1,1-difluoroethene (HCFC-1122). For the purpose of convenience, methods according to this paragraph are sometime referred to herein as Method 9.

The invention also provides a gas phase process for the production of CTFE comprising reacting in the gas phase 1,1,2-trichloro-1,2,2-trifluoroethane ($CF_2Cl$—$CFCl_2$; CFC-113) and an alkane having from 1 to 6 carbon atoms in the presence of a catalyst. For the purpose of convenience, methods according to this paragraph are sometime referred to herein as Method 10. For the purpose of convenience, alkanes having from 1 to 6 carbon atoms are referred to herein for convenience as "C1-C6" alkanes.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 6 carbon atoms; and (b) reacting said reaction mixture in the presence of a catalyst. For the purpose of convenience, methods according to this paragraph are sometime referred to herein as Method 11.

The invention also provides a gas phase process for the production of CTFE comprising: (a) providing a reaction mixture comprising of 1,1,2-trichloro-1,2,2-trifluoroethane ($CF_2Cl$—CFCl2; CFC-$_{113}$) and a C1-C6 alkane; and (b) reacting said reaction mixture in the presence of a catalyst at a temperature of from about 400° C. to about 600° C. For the purpose of convenience, methods according to this paragraph are sometime referred to herein as Method 12.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 6 carbon atoms; and (b) reacting said reaction mixture in the presence of a catalyst to produce a reaction product that comprises at least about 74% of CTFE and is substantially free of 2-chloro-1,1-difluoroethene (HCFC-1122). For the purpose of convenience, methods according to this paragraph are sometime referred to herein as Method 13.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 3 carbon atoms; and (b) reacting said reaction mixture in the presence of a catalyst at a temperature of from about 400° C. to about 600° C. to produce a reaction product that comprises at least about 74% of CTFE and is substantially free of 2-chloro-1,1-difluoroethene (HCFC-1122). For the purpose of convenience, methods according to this paragraph are sometime referred to herein as Method 14.

The invention also provides a gas phase process for the production of CTFE comprising: (a) providing a reaction mixture comprising of 1,1,2-trichloro-1,2,2-trifluoroethane ($CF_2Cl$—$CFCl_2$; CFC-113) and an alkane having from 1 to 6 carbon atoms; and (b) reacting said reaction mixture in the presence of a catalyst at a temperature of from about 400° C. to about 600° C. to produce a reaction product that comprises at least about 74% of CTFE and is substantially free of 2-chloro-1,1-difluoroethene (HCFC-1122). For the purpose of convenience, methods according to this paragraph are sometime referred to herein as Method 15.

The methods of the present invention, including each of Methods 1-15, preferably use a catalyst that comprises one or more of transition metal oxides, transition metal chlorides and transition metal fluorides. For the purpose of convenience, catalysts according to this paragraph are sometime referred to herein as Catalyst 1.

The methods of the present invention, including each of Method 1-15, preferably use a catalyst that comprises $Fe_2O_3$ and/or NiO. For the purpose of convenience, catalysts according to this paragraph are sometime referred to herein as Catalyst 2.

The methods of the present invention, including each of Method 1-15, preferably use a catalyst that comprises $Fe_2O_3$ and/or NiO supported on carbon or activated carbon. For the purpose of convenience, catalysts according to this paragraph are sometime referred to herein as Catalyst 3.

The methods of the present invention, including each of Method 1-15, preferably use a catalyst that comprises a transition metal fluoride. For the purpose of convenience, catalysts according to this paragraph are sometime referred to herein as Catalyst 4.

The methods of the present invention, including each of Method 1-15, preferably use a catalyst that comprises a transition metal chloride. For the purpose of convenience, catalysts according to this paragraph are sometime referred to herein as Catalyst 5.

The methods of the present invention, including each of Methods 1-15, and including each of Methods 1-15 with each of Catalysts 1-5, achieve a conversion of the perhaloalkane of at least about 30%.

The methods of the present invention, including each of Methods 1-15, and including each of Methods 1-15 with each of Catalysts 1-5, achieve a conversion of the perhaloalkane of at least about 40%.

The methods of the present invention, including each of Methods 1-15, and including each of Methods 1-15 with each of Catalysts 1-5, achieve a conversion of the perhaloalkane of at least about 50%.

The methods of the present invention, including each of Methods 1-15, and including each of Methods 1-15 with each of Catalysts 1-5, achieve a conversion of the perhaloalkane of at least about 60%.

The methods of the present invention, including each of Methods 1-15, and including each of Methods 1-15 with each of Catalysts 1-5, achieve a conversion of the perhaloalkane of at least about 70%.

The methods of the present invention, including each of Methods 1-15, and including each of Methods 1-15 with each of Catalysts 1-5, achieve a conversion of the perhaloalkane of at least about 80%.

The methods of the present invention, including each of Methods 1-15, and including each of Methods 1-15 with each of Catalysts 1-5, are carried out continuously in preferred embodiments.

DETAILED DESCRIPTION OF THE INVENTION

The present invention provides a process for producing a haloethylene, and particularly perhaloethylenes, by the dechlorination of the haloethane comprising reacting in the gaseous phase the haloethane and one or more of an alkene, an alkane in the presence of a catalyst. The gas phase process preferably involves the vicinal dechlorination of the haloethane in the presence of the catalyst to provide a haloethylene.

In an aspect of the invention, an alkane and/or an alkene is used in the gas phase reaction to react with the chlorine produced by the dechlorination.

The haloethane starting material has two or more chlorine atoms on adjacent carbon atoms, which are eliminated during the gas-phase dechlorination process. In preferred aspects of the process, the haloethane starting material is a perhaloethane having at least two chlorine atoms on adjacent carbons, and the remaining halogens are fluorine atoms. In preferred aspects of the process, the haloethane is a perhaloethane according to the formula:

$$CF_aCl_b\text{—}CF_dCl_f$$

wherein
  a is 0 to 3, b is 1 to 3, and a+b=3;
  d is 0 to 3, f is 1 to 3, and d+f=3; and
  b+f is 2 to 6.

Preferred perhaloethanes include 1,2-dichlorotetrafluoroethane (fluorocarbon 114) and 1,1,2-trichloro-1,2,2-trifluoroethane (fluorocarbon 113), with 1,1,2-trichloro-1,2,2-trifluoroethane being particularly preferred. When two chlorines are removed from these preferred halohydrocarbons, the products are perhaloethylenes including, for example, tetrafluoroethylene or CTFE.

The gas-phase process produces a haloethylene, and preferably a perhaloethylene. In preferred aspects of the process, the product is a perhaloethylene according to the formula:

$$CF_mCl_n\text{=}CF_xCl_y$$

wherein
  m is 0 to 2, n is 0 to 2, and m+n=2; and
  x is 0 to 2, y is 0 to 2, and x+y=2.

In addition to the haloethane starting material, the reaction mixture preferably includes a compound that that reacts under the reaction conditions with the chlorine ($Cl_2$) that is formed by the dechlorination reaction. For the purposes of convenience, such a compound is sometimes referred to herein as a chlorine scavenger. The chlorine scavenger in preferred embodiments is comprises one or more of an alkane or an alkene.

In certain embodiments it is preferred that the chlorine scavenger comprises methane since the use of methane produces excellent selectivity results. When used, alkanes preferably have 1 to 6 carbon atoms, and more preferably 1 to 4 carbon atoms. When used, preferred alkanes include methane, ethane, propane, butane, isobutane, pentane, hexane, and the like, and particularly methane, ethane, propane and isobutene, most particularly methane. When used, the alkane may be a cycloalkane such as cyclopentane and cyclohexane.

When used, alkenes have from 2 to 6 carbon atoms, and more preferably 2 or 3 carbon atoms. Alkenes for use as chlorine scavengers in the dechlorination reaction include ethylene, propylene, butylene, pentene, and the like. Alternatively, the alkene may be a cycloalkene such as cyclopentene and cyclohexene.

The present methods, including each of Methods 1-15, include those processes in which the molar ratio of the haloethane starting material (e.g., CFC-113) to the chlorine scavenger is preferably between about 1:1 to about 1:10, with between about 1:1 to about 1:3 being more preferred.

The present methods, including each of Methods 1-15, include those processes in which the molar ratio of the haloethane starting material (e.g., CFC-113) to the chlorine scavenger comprising one or more of alkane or alkene, preferably a C1-C6 alkane and or more preferably C1-C3 alkane, is preferably between about 1:1 to about 1:10, with between about 1:1 to about 1:3 being more preferred.

The catalyst materials include in preferred embodiments transition metal oxides, chlorides and fluorides. The transition metal when used is preferably selected from one or more of a group 8, group 9, or group 10 transition metal cation. The transition metal of the catalyst is preferably selected from Fe, Ru, Co, Rh, Ni, Pd, Pt, Cu and Ag.

The catalyst materials include transition metal oxides such as iron (III) oxide, nickel (II) oxide, copper (II) oxide, and mixtures thereof. They also include transition metal fluorides and chlorides and such as copper (II) chloride, copper (II) fluoride, iron (III) chloride and iron (III) fluoride.

More preferred are the iron compounds at valence state 3, including iron (III) oxide, nickel (II) compounds including NiO, and mixtures thereof, as well as copper (II) compounds including CuO, $CuF_2$ and $CuCl_2$.

The catalyst may be used on a support. Preferred supports include carbon, which may either pellet or granular type which are commercially available. Catalyst loading on the support may be from about 2% to about 25%, or from about 5% to about 20% on the support.

Especially preferred combinations of catalyst and support include iron (III) oxide/nickel (II) oxide on carbon, iron (III) oxide/copper (II) oxide on carbon, copper (II) fluoride on carbon and copper (II) chloride on carbon.

The catalyst may be optionally regenerated in situ. Regeneration of the catalyst may be accomplished by passing an oxidizing agent over the catalyst, for example, by passing air or oxygen, optionally diluted with nitrogen, over the catalyst. Regeneration may be performed at temperatures of from about 400° C. to about 650° C., preferably from about 500° C. to about 625° C., and for about 4 hours to about 48 hours, depending on the size of the reactor.

This reaction may be conducted in any reactor suitable for a vapor phase dechlorination reaction. Preferably, the reactor is constructed from materials that are resistant to the corrosive effects of chlorine, catalyst, or byproducts, such as stainless steel, Hastalloy, Inconel, Monel and vessels lined with fluoropolymers.

The present methods, including each of Methods 1-15, include those processes in which an inert diluent is used with the dechlorination reaction. The inert diluent in such cases is preferably any material that is in the vapor phase under the reaction conditions and is non-reactive to any of the components present in the reactor during the dechlorination reaction. The inert diluent may include nitrogen or the like.

The temperature range for the dechlorination may vary depending on the combination of catalyst, haloethane starting material and alkane/alkene. In order to have the dechlorination reaction occur in the gaseous phase, the temperature and pressure should be such that all reactants are in the vapor phase. Also, temperatures at or above the decomposition temperatures of reactants and products should be avoided.

Preferred temperatures for the dechlorination reaction are between about 300° C. and about 650° C., with about 400° C. and about 600° C. being more preferred, and between about 450° C. and about 600° C. being more preferred, and between about 500° C. and about 600° C. being most preferred. The temperature for the gas-phase dechlorination reaction may be above 500° C., or above about 550° C. and up to about 600° C.

The present methods, including each of Methods 1-15, include those processes in which the contact time is sufficiently long to allow the reactants contact with the catalyst for reaction to occur. The present methods, including each of Methods 1-15, thus include those processes in which contact time is from about 1 to about 6 seconds, with 3 to 5 seconds being more preferred.

The present methods, including each of Methods 1-15, include those processes in which the haloalkane is produced with good selectivity, and in particular in which the selectivity to the haloalkane product is preferably greater than about 75%, or the selectivity is preferably greater than about 80%, or the selectivity is preferably greater than about 85%, or the selectivity is preferably greater than about 90%.

The conversion of the starting haloalkane by the dechlorination process is very good. The conversion is from about 30% to about 95%, or from about 50% to about 95%.

Aspects of the Invention

Aspect 1. A process for the production of a haloethylene, and preferably an perhaloethylene, comprising the gas-phase dechlorination of a haloethane, preferably a perhaloethane, in the presence of a catalyst, wherein the haloethane or perhaloethane comprises at least two chlorine atoms on adjacent carbon atoms, and wherein the catalyst is selected from (a) transition metal oxides such as iron (III) oxide, nickel (II) oxide, copper (II) oxide, and mixtures thereof, and (b) transition metal fluorides and chlorides such as copper (II) chloride and copper (II) fluoride.

Aspect 2. A process for the production of a haloethylene having the formula:

$$CF_mCl_n=CF_xCl_y$$

wherein
m is 0 to 2, n is 0 to 2, and m+n=2; and
x is 0 to 2, y is 0 to 2, and x+y=2;
comprising the gas-phase dechlorination of a haloethane having the formula:

$$CF_mCl_n=CF_xCl_y$$

wherein
m is 0 to 2, n is 0 to 2, and m+n=2; and
x is 0 to 2, y is 0 to 2, and x+y=2;
in the presence of a catalyst selected from (a) transition metal oxides such as iron (III) oxide, nickel (II) oxide, copper (II) oxide, and mixtures thereof, and (b) transition metal fluorides and chlorides such as copper (II) chloride and copper (II) fluoride.

Aspect 3. A process for the production of a haloethylene, and preferably an perhaloethylene, comprising the gas-phase dechlorination of a haloethane, preferably a perhaloethane, in the presence of a catalyst and an alkane or alkene, wherein the haloethane or perhaloethane comprises at least two chlorine atoms on adjacent carbon atoms, and wherein the catalyst is selected from (a) transition metal oxides such as iron (III) oxide, nickel (II) oxide, copper (II) oxide, and mixtures thereof, and (b) transition metal fluorides and chlorides such as copper (II) chloride and copper (II) fluoride.

Aspect 4. A process for the production of a haloethylene having the formula:

$$CF_mCl_n=CF_xCl_y$$

wherein
m is 0 to 2, n is 0 to 2, and m+n=2; and
x is 0 to 2, y is 0 to 2, and x+y=2;
comprising the gas-phase dechlorination of a haloethane having the formula:

$$CF_mCl_n=CF_xCl_y$$

wherein
m is 0 to 2, n is 0 to 2, and m+n=2; and
x is 0 to 2, y is 0 to 2, and x+y=2;
in the presence of an alkane or alkene, and a catalyst selected from (a) transition metal oxides such as iron (III) oxide, nickel (II) oxide, copper (II) oxide, and mixtures thereof, and (b) transition metal fluorides and chlorides such as copper (II) chloride and copper (II) fluoride.

Aspect 5. The process according to any one of aspects 1 to 4, wherein the catalyst is on a carbon support.

Aspect 6. The process according to any one of aspects 1 to 5, wherein the catalyst comprises $Fe_2O_3$, NiO, CuO, $CuF_2$, $CuCl_2$, and mixtures thereof Aspect 7. The process according to any one of aspects 1 to 6, wherein the catalyst is selected from $Fe_2O_3$/NiO on carbon, $Fe_2O_3$/CuO on carbon, $CuF_2$ on carbon and $CuCl_2$ on carbon.

Aspect 8. The process according to any one of aspects 1 to 7, wherein the dechlorination reaction comprises an alkane having 1 to 6 carbon atoms, and preferably 1 to 4 carbon atoms.

Aspect 9. The process according to any one of aspects 1 to 8, wherein the dechlorination reaction comprises an alkane selected from the group consisting of methane, ethane, propane, butane, isobutane, pentane, hexane, cyclopentane and cyclohexane, particularly propane.

Aspect 10. The process according to any one of aspects 1 to 9, wherein the molar ratio of the haloethane starting material to the alkane is between about 1:1 to about 1:10, with between about 1:1 to about 1:3 being more preferred.

Aspect 11. The process according to any one of aspects 1 to 7, wherein the dechlorination reaction comprises an alkene having 2 to 6 carbon atoms, and preferably 2 to 4 carbon atoms.

Aspect 12. The process according to any one of aspects 1 to 7, wherein the dechlorination reaction comprises an alkene selected from the group consisting of ethylene, propylene, butylene, pentene, cyclopentene and cyclohexene.

Aspect 13. The process according to any one of aspects 1 to 7, 11 or 12, wherein the molar ratio of the haloethane starting material to the alkene is between about 1:1 to about 1:10, with between about 1:1 to about 1:3 being more preferred.

Aspect 14. The process according to any one of aspects 1 to 13, wherein the dechlorination reaction is at a temperature of between about 400° C. and about 650° C.

Aspect 15. The process according to any one of aspects 1 to 13, wherein the dechlorination reaction is at a temperature of between about 450° C. and about 600° C.

Aspect 16. The process according to any one of aspects 1 to 13, wherein the dechlorination reaction is at a temperature of between about 500° C. and about 600° C.

Aspect 17. The process according to any one of aspects 1 to 13, wherein the dechlorination reaction is at a temperature above 500° C., or above about 550° C. and up to about 600° C.

Aspect 18. The process according to any one of aspects 1 to 17, wherein the dechlorination reaction further comprises a diluent gas.

Aspect 19. The process according to aspect 18, wherein the diluent gas comprises nitrogen ($N_2$) gas.

Aspect 20. The process according to any one of aspects 1 to 19, wherein the dechlorination reaction affords the haloalkane product with a selectivity greater than about 75%.

Aspect 21. The process according to any one of aspects 1 to 19, wherein the dechlorination reaction affords the haloalkane product with a selectivity greater than about 80%.

Aspect 22. The process according to any one of aspects 1 to 19, wherein the dechlorination reaction affords the haloalkane product with a selectivity greater than about 85%.

Aspect 23. The process according to any one of aspects 1 to 19, wherein the dechlorination reaction affords the haloalkane product with a selectivity greater than about 90%.

Aspect 24. A process for the production of a chlorotrifluoroethylene (CTFE), comprising the gas-phase dechlorination of 1,1,2-trichloro-1,2,2-trifluoroethane (CFC-113) in the presence of a catalyst and, optionally, an alkane or alkene, wherein the catalyst is selected from (a) transition metal oxides such as iron (III) oxide, nickel (II) oxide, copper (II) oxide, and mixtures thereof, and (b) transition metal fluorides and chlorides such as copper (II) chloride and copper (II) fluoride.

Aspect 25. The process according to aspect 24, wherein the catalyst is on a carbon support.

Aspect 26. The process according to aspects 24 or 25, wherein the catalyst comprises $Fe_2O_3$, NiO, CuO, $CuF_2$, $CuCl_2$, and mixtures thereof.

Aspect 27. The process according to any one of aspects 24 to 26, wherein the catalyst is selected from $Fe_2O_3$/NiO on carbon, $Fe_2O_3$/CuO on carbon, $CuF_2$ on carbon and $CuCl_2$ on carbon.

Aspect 28. The process according to any one of aspects 24 to 27, wherein the dechlorination reaction comprises an alkane having 1 to 6 carbon atoms, and preferably 1 to 6 carbon atoms.

Aspect 29. The process according to any one of aspects 24 to 28, wherein the dechlorination reaction comprises an alkane selected from the group consisting of methane, ethane, propane, butane, isobutane, pentane, hexane, cyclopentane and cyclohexane, particularly propane.

Aspect 30. The process according to any one of aspects 24 to 29, wherein the molar ratio of the CFC-113 starting material to the alkane is between about 1:1 to about 1:10, with between about 1:1 to about 1:3 being preferred.

Aspect 31. The process according to any one of aspects 24 to 27, wherein the dechlorination reaction comprises an alkene having 2 to 6 carbon atoms, and preferably 2 to 4 carbon atoms.

Aspect 32. The process according to any one of aspects 24 to 27, wherein the dechlorination reaction comprises an alkene selected from the group consisting of ethylene, propylene, butylene, pentene, cyclopentene and cyclohexene.

Aspect 33. The process according to any one of aspects 24 to 27, 31 or 32, wherein the molar ratio of the CFC-113 starting material to the alkene is between about 1:1 to about 1:10, with between about 1:1 to about 1:3 being preferred.

Aspect 34. The process according to any one of aspects 24 to 33, wherein the dechlorination reaction is at a temperature of between about 400° C. and about 650° C.

Aspect 35. The process according to any one of aspects 24 to 33, wherein the dechlorination reaction is at a temperature of between about 450° C. and about 600° C.

Aspect 36. The process according to any one of aspects 24 to 33, wherein the dechlorination reaction is at a temperature of between about 500° C. and about 600° C.

Aspect 37. The process according to any one of aspects 24 to 33, wherein the dechlorination reaction is at a temperature above 500° C., or above about 550° C. and up to about 600° C.

Aspect 38. The process according to any one of aspects 24 to 37, wherein the dechlorination reaction further comprises a diluent gas.

Aspect 39. The process according to aspect 38, wherein the diluent gas comprises nitrogen ($N_2$) gas.

Aspect 40. The process according to any one of aspects 24 to 39, wherein the dechlorination reaction affords the CTFE product with a selectivity greater than about 75%.

Aspect 41. The process according to any one of aspects 24 to 39, wherein the dechlorination reaction affords the CTFE product with a selectivity greater than about 80%.

Aspect 42. The process according to any one of aspects 24 to 39, wherein the dechlorination reaction affords the CTFE product with a selectivity greater than about 85%.

Aspect 43. The process according to any one of aspects 24 to 39, wherein the dechlorination reaction affords the CTFE product with a selectivity greater than about 90%.

The following non-limiting examples serve to illustrate certain embodiments of the invention but are not to be construed as limiting. Variations and additional or alternative embodiments will be readily apparent to the skilled artisan on the basis of the disclosure provided herein.

EXAMPLES

A mixture of $CF_2Cl$—$CFCl_2$ (R-113) and ethylene, propane or methane (1:3 to 1:1 molar ratio) were fed to a heated Monel tube (0.5"×8" dimension) (in a furnace) containing catalyst (10.8 cm$^3$) bed. The contact time (CT) used were 3-5 seconds. Catalysts used were $FeCl_3$ on $Al_2O_3$, $CuCl_2$, $Fe_2O_3$/NiO (12:0.5) mixture, $CuF_2$, and $Fe_2O_3$/CuO (6:0.5) on carbon support. The carbon support can be either pellet or granular type which are commercially available. Typical catalyst loadings were 5-20% on support. Temperature ranged from 480 to 600° C. Ethylene, propane and methane were used to scavenge chlorine generated. The exit gases from the reactor were passed through water (20 mL) and a drying column ($CaCl_2$, Drierite), and collected in a Tedlar® gas bag for analysis by GC/GC-MS. Experimental data are summarized in Tables 1-3, below:

TABLE 1

Gas phase dechlorination of $CF_2Cl$—$CFCl_2$ to CTFE with ethylene

| Run No | Catalyst | T (° C.) | CT (sec) | Ratio (113 to $C_2H_4$) | % Selectivity CTFE | % Conv. of 113 |
|---|---|---|---|---|---|---|
| 1 | $FeCl_3/Al_2O_3$ | 480 | 3 | 1:3 | 28.7 | 46 |
| 2 | $FeCl_3/Al_2O_3$ | 480 | 3 | 1:0 | 7 | 49 |
| 3 | $CuCl_2/C$ | 500 | 3 | 1:3 | 90.5 | 40.5 |
| 4 | $CuCl_2/C$ | 550 | 3 | 1:3 | 92 | 17.3 |
| 5 | $CuCl_2/C$ | 600 | 3 | 1:3 | 88 | 44.6 |
| 6 | $Fe_2O_3/NiO/C$ | 480 | 3 | 1:3 | 95.1 | 24.5 |
| 7 | $Fe_2O_3/NiO/C$ | 500 | 3 | 1:3 | 91.5 | 9 |
| 8 | $CuF_2/C$ | 480 | 3 | 1:3 | 92.8 | 34 |
| 9 | $CuF_2/C$ | 500 | 3 | 1:3 | 94.3 | 24.4 |

As can be seen from Table I, selectivity of CTFE ($CF_2$=CFCl) ranged from 8 to 95% depending on the conditions and catalyst used. For example, among the catalysts, $Fe_2O_3/NiO$ on C gave best results, providing $CF_2=CFCl$ (CTFE) in 95% selectivity whereas $FeCl_3/Al_2O_3$ catalyst gave very poor selectivity of CTFE (9 to 28%), the major product being the undesired $CF_2=CCl_2$ (in 56 and 79%, respectively for runs 1-2). Some by-products formed for runs 1-9 were $CF_2=CCl_2$, $CFCl=CCl_2$, $CH_2Cl—CH_2Cl$, and $CH_2=CHCl$.

TABLE 2

Gas phase dechlorination of $CF_2Cl—CFCl_2$ to CTFE with propane

| Run No | Catalyst | T (° C.) | CT (sec) | Ratio (113 to $C_3H_6$) | % Selectivity CTFE | % Conv. of 113 |
|---|---|---|---|---|---|---|
| 1 | $CuCl_2$/C | 500 | 3 | 1:3 | 79 | 7 |
| 2 | same | 500 | 5 | 1:3 | 83 | 6 |
| 3 | $Fe_2O_3$/NiO/C | 500 | 3 | 1:3 | 91 | 34 |
| 4 | " | 550 | 3 | " | 95 | 55 |
| 5 | " | 600 | 3 | " | 96 | 83 |
| 6 | " | 600 | 5 | " | 94.2 | 85.3 |
| 7 | " | 600 | 3 | neat | 94 | 95 |

Propane appears to work well compared to ethylene and methane. Excellent selectivity for CTFE was observed with catalyst $Fe_2O_3$/NiO on C (runs 4-7 in Table 2). Note that in the absence of hydrocarbons (run 7, Table 2) also the reaction works well. Major by-products identified were $CF_2=CCl_2$, $CF_2Cl—CFHCl$, $CF_2CHCl$ and polychlorinated propane.

TABLE 3

Gas phase dechlorination of $CF_2Cl—CFCl_2$ to CTFE with methane

| Run No | Catalyst | T (° C.) | CT (sec) | Ratio (113 to $CH_4$) | % Selectivity CTFE | % Conv. of 113 |
|---|---|---|---|---|---|---|
| 1 | $Fe_2O_3$/NiO/C | 600 | 3 | 1:3 | 76 | 52 |
| 2 | " | 600 | 3 | 1:1 | 78 | 54 |
| 3 | " | 600 | 5 | 1:3 | 76 | 55 |
| 4 | $Fe_2O_3$/NiO/C | 600 | 3 | 1:3 | 92 | 58 |
| 5 | " | 600 | 3 | 1:1 | 87 | 44 |
| 6 | $Fe_2O_3$/NiO/ C (granular) | 600 | 3 | 1:1 | 94 | 86 |
| 7 | $Fe_2O_3$/NiO/ C (granular) | 600 | 3 | 1:1 | 92 | 50 |

For runs 4-7, the catalyst was regenerated by passing air over the catalyst bed at 600° C. for 6 hours and as a result selectivity could be improved. Major by-products identified were $CH_3Cl$, $CF_2=CCl_2$, $CH_2Cl_2$, $CF_2Cl—CH_2Cl$ and $CCl_2=CCl_2$.

In summary, for gas phase dechlorination of $CF_2Cl—CFCl_2$ the catalysts Fe2O3/NiO on C gave good results, with CTFE being obtained consistently with a selectivity of about 90% or greater.

The invention claimed is:

1. A process for the production of a haloethylene, the process consisting essentially of the gas-phase dechlorination of a haloethane in the presence of a catalyst and, optionally, an alkane, wherein the haloethane comprises at least two chlorine atoms on adjacent carbon atoms, and wherein the catalyst comprises (a) transition metal oxides and/or (b) transition metal fluorides and chlorides.

2. A process for the production of a haloethylene having the formula:

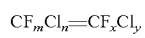

$$CF_mCl_n=CF_xCl_y$$

wherein m is 0 to 2, n is 0 to 2, and m+n=2; and x is 0 to 2, y is 0 to 2, and x+y=2;

the process consisting essentially the gas-phase dechlorination of a haloethane having two or more chlorine atoms on adjacent carbon atoms in the presence of an alkane, and a catalyst comprising (a) transition metal oxides, and/or (b) transition metal fluorides and chlorides.

3. The process according to claim 2, wherein the catalyst comprises $Fe_2O_3$, NiO, CuO, $CuF_2$, $CuCl_2$, and mixtures thereof.

4. The process according to claim 1, wherein the catalyst is selected from $Fe_2O_3$/NiO on carbon, $Fe_2O_3$/CuO on carbon, $CuF_2$ on carbon and $CuCl_2$ on carbon.

5. The process according to a claim 2, wherein the dechlorination reaction comprises an alkane having 1 to 6 carbon atoms.

6. The process according to claim 2, wherein the dechlorination reaction temperature is from about 400° C. and about 650° C.

7. The process according to claim 6, wherein the gas-phase dechlorination occurs in the presence of a diluent gas.

8. The process according to claim 2, wherein the dechlorination reaction affords the haloethylene product with a selectivity of about 75% or greater.

9. A process for the production of a chlorotrifluoroethylene (CTFE), the process consisting essentially of the gas-phase dechlorination of 1,1,2-trichloro-1,2,2-trifluoroethane (CFC-113) in the presence of a catalyst and optionally a C1-C6 alkane, wherein the reaction temperature is from about 300° C. to about 650° C. and has a selectivity of at least about 75%, and wherein the catalyst is selected from (a) transition metal oxides, and (b) transition metal fluorides and chlorides.

10. The process according to claim 9, wherein the catalyst comprises $Fe_2O_3$, NiO, CuO, $CuF_2$, $CuCl_2$, and mixtures thereof.

11. The process according to claim 10, wherein the catalyst is selected from $Fe_2O_3$/NiO on carbon, $Fe_2O_3$/CuO on carbon, $CuF_2$ on carbon and $CuCl_2$ on carbon.

12. The process according to claim 10, wherein the dechlorination reaction occurs in the presence of an alkane having 1 to 3 carbon atoms.

13. The process according to claim 12, wherein the dechlorination reaction further occurs in the presence of a diluent gas.

14. The process according to claim 11, wherein the reaction temperature is from about 400° C. to about 650° C. and has a selectivity of at least about 85, and wherein said alkane is present and comprises methane.

15. The process according to claim 14 wherein said process produces a reaction product that comprises at least about 74% of CTFE.

16. The process according to claim 9 wherein said catalyst comprises a combination of an iron oxide and a nickel oxide.

17. The process according to claim 9 wherein said catalyst consists essentially of an iron oxide and a nickel oxide.

18. The process according to claim 9 wherein said catalyst comprises a combination of $Fe_2O_3$ and NiO.

19. The process according to claim 1 wherein said dechlorination produces a reaction product that is free of 2-chloro-1,1-difluoroethene (HCFC-1122).

20. The process of claim 1 wherein the process consists of the gas-phase dechlorination of a haloethane in the presence of a catalyst and, optionally, an alkane, wherein the haloethane comprises at least two chlorine atoms on adjacent carbon atoms, and wherein the catalyst comprises (a) transition metal oxides and/or (b) transition metal fluorides and chlorides.

* * * * *